(12) United States Patent
Farrand

(10) Patent No.: US 6,514,578 B1
(45) Date of Patent: Feb. 4, 2003

(54) POLYMERIZABLE MESOGENIC TOLANES

(75) Inventor: Louise Diane Farrand, Manchester (GB)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 134 days.

(21) Appl. No.: 09/598,449

(22) Filed: Jun. 22, 2000

(30) Foreign Application Priority Data

Jun. 30, 1999 (EP) .............................. 99112455

(51) Int. Cl.[7] .................. C09K 19/34; C09K 19/32; C09K 19/30; C09K 19/20; C09K 19/12; C07C 69/86

(52) U.S. Cl. .................. 428/1.1; 428/1.2; 428/1.3; 428/1.5; 252/299.61; 252/299.62; 252/299.63; 252/299.64; 252/299.65; 252/299.66; 560/64; 560/65

(58) Field of Search ............. 252/299.01, 299.62, 252/299.66, 299.67, 299.64, 299.65, 299.61, 299.63; 428/1.1, 1.2, 1.3, 1.5; 560/64, 65

(56) References Cited

U.S. PATENT DOCUMENTS 5,506,704 A    4/1996   Broer et al. ............... 359/63

FOREIGN PATENT DOCUMENTS

| EP | 0 397 263 A1 | 11/1990 |
| EP | 0 659 685 A1 | 6/1995 |
| JP | 11-147853 * | 6/1999 |
| WO | WO 97/35219 | 9/1997 |
| WO | WO 98/00475 | 1/1998 |
| WO | WO 98/04651 | 2/1998 |
| WO | WO 98/12584 | 3/1998 |
| WO | WO 98/52905 | 11/1998 |

OTHER PUBLICATIONS

CAPLUS 1997: 224174.*
Abstract of Japanese Patent No. 11–47853.
Abstract of Japanese Patent No. 11–080090.
Abstract of Japanese Patent No. 08–231958.
Abstract of Japanese Patent No. 07–109351.
Abstract of Japanese Patent No. 07–017910.

* cited by examiner

Primary Examiner—Shean C. Wu
(74) Attorney, Agent, or Firm—Millen, White, Zelano & Branigan, PC

(57) ABSTRACT

Polymerizable tolanes of formula I

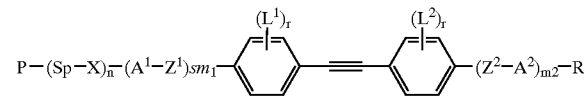

wherein P, Sp, X, n, $A^1$, $A^2$, $Z^1$, $Z^2$, m1, m2, $L^1$, $L^2$, r and R have the meanings defined herein, polymerizable liquid crystal compositions comprising at least one compound of formula I, linear or crosslinked liquid crystal polymers obtainable from these compounds and compositions, are suitable for use in optical elements such as polarizers, retardation and compensation films, alignment layers, color filters or holographic elements. They are also suitable for use in liquid crystal displays such as PDLC, polymer gel or polymer stabilized cholesteric texture (PSCT) displays, as well as for use in adhesives, synthetic resins with anisotropic mechanical properties, cosmetics, diagnostics or liquid crystal pigments, for decorative and security applications, and for nonlinear optics or optical information storage.

55 Claims, No Drawings

POLYMERIZABLE MESOGENIC TOLANES

The invention relates to polmyerizable mesogenic tolanes, to polymerizable liquid crystal compositions comprising the polymerizable mesogenic tolanes, to linear or crosslinked liquid crystal polymers obtainable from the polymerizable mesogenic tolanes and the compositions comprising them, and to the use of the polymerizable mesogenic tolanes, and the polymerizable compositions and polymers obtained thereof in optical elements, liquid crystal displays, adhesives, synthetic resins with anisotropic mechanical properties, cosmetics, diagnostics, liquid crystal pigments, decorative and security applications, nonlinear optics and optical information storage.

Polymerizable mesogenic compounds, which are also known as reactive mesogenic compounds, have been described in prior art for various purposes. For example, they can be aligned in their liquid crystal phase and subsequently polymerized in situ, to give linear or crosslinked liquid crystal polymer films with uniform orientation of high quality. These films can be used for example as optical elements, like polarization filters as described in EP 0 397 263, broadband circular polarizers as described in EP 0 606 940 and WO 97/35219, or compensation or retardation films as described in WO 98/00475, WO 98/04651 or WO 98/12584.

The polymerizable mesogenic compounds described in prior art, however, do often exhibit liquid crystalline phases only in a small temperature range or do not show mesophase behavior at all. Furthermore, polymerizable mesogenic compounds of prior art do often exhibit only low or moderate values of the birefringence.

When preparing oriented liquid crystal polymer films for the uses as described above, it is especially desired to have available polymerizable compositions exhibiting a nematic liquid crystal phase at room temperature, so that it is possible to carry out alignment and polymerization of the composition at low temperatures. For this purpose, it is advantageous if the single polymerizable components exhibit broad liquid crystalline phases, too.

Thus, there is a demand for polymerizable mesogenic compounds with a broad liquid crystalline phase and a high birefringence, which can be used for the preparation of oriented liquid crystal polymer films for optical applications.

Furthermore, regarding the broad range of applications for polymerizable mesogenic compounds it is desirable for the expert to have available further compounds of this type which are easy to synthesize and fulfill the various requirements as described above.

It was an aim of the invention to provide polymerizable mesogenic compounds with advantageous properties, thus extending the pool of reactive mesogenic compounds available to the expert. Other aims of the present invention are immediately evident to the person skilled in the art from the following detailed description.

Upon further study of the specification and appended claims, further objects and advantages of this invention will become apparent to those skilled in the art.

It was now found that these aims can be achieved by providing polymerizable mesogenic tolanes according to the present invention.

Polymerizable mesogenic compounds comprising a tolane group are disclosed in WO 98/52905, EP 0 659 865, JP 11-147853, JP 11-080090, JP 08-231958, JP 07-109351 and JP 07-017910.

The terms reactive or polymerizable mesogenic compound as used in the foregoing and the following comprise compounds with a rod-shaped, board-shaped or disk-shaped mesogenic group, i.e. a group with the ability to induce mesophase behavior. These compounds do not necessarily have to exhibit mesophase behavior by themselves. It is also possible that these compounds show mesophase behavior only in mixtures with other compounds or when the polymerizable mesogenic compounds or the mixtures comprising them are polymerized.

One object of the present invention are polymerizable mesogenic tolanes of formula I

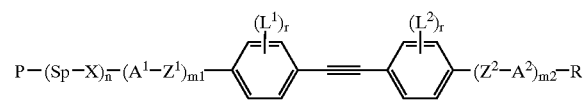

wherein

P is $CH_2=CW-COO-$, $WCH=CH-O-$,

or $CH_2=CH-$ Phenyl-$(O)_k-$ with W being H, $CH_3$ or Cl and k being 0 or 1,

Sp is a spacer group having 1 to 25 C atoms,

X is $-O-$, $-S-$, $-CO-$, $-COO-$, $-OCO-$, $-CO-NH-$, $-NH-CO-$, $-CH_2CH_2-$, $-OCH_2-$, $-CH_2O-$, $-SCH_2-$, $-CH_2S-$, $-CH=CH-$, $-CH=CH-COO-$, $-OCO-CH=CH-$, $-C\equiv C-$, or a single bond, n is 0 or 1, $Z^1$ and $Z^2$ are each independently $-COO-$, $-OCO-$, $-CH_2CH_2-$, $-OCH_2-$, $-CH_2O-$, $-CH=CH-$, $-CH=CH-COO-$, $-OCO-CH=CH-$, $-C\equiv C-$, or a single bond, $A^1$ and $A^2$ are each independently 1,4-phenylene in which, in addition, one or more CH groups may be replaced by N, 1,4-cyclohexylene in which, in addition, one or two non-adjacent $CH_2$ groups may be replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, it being possible for all these groups to be unsubstituted, mono- or polysubstituted with F, Cl, OH, CN, $NO_2$ or alkyl, alkoxy or alkanoyl groups having 1 to 7 C atoms wherein one or more H atoms may be replaced by F or Cl, m1 and m2 are each independently 0, 1 or 2, with m1+m2<3, $L^1$ and $L^2$ are each independently F, Cl, CN, OH, $NO_2$ or an alkyl, alkoxy or alkanoyl group having 1 to 7 C atoms wherein one or more H atoms may be substituted by F or Cl, r is in each case independently 0, 1, 2, 3 or 4, R is H, CN, halogen or a straight-chain or branched alkyl radical with up to 25 C atoms which may be unsubstituted, mono- or polysubstituted by halogen or CN, it being also possible for one or more non-adjacent $CH_2$ groups to be replaced, in each case independently from one another, by $-O-$, $-S-$, $-NH-$, $-N(CH_3)-$, $-CO-$, $-COO-$, $-OCO-$, $-OCO-O-$, $-S-CO-$, $-CO-S-$ or —C≡C— in such a manner that oxygen atoms are not linked directly to one another, or alternatively R is P—(Sp—X)$_n$—.

with the provisos that a) in case P is CH$_2$=CW—COO— or

and m1+m2 is 0, then R is P—(Sp—X)$_n$— and/or at least one r is different from 0, b) in case P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then R is P—(Sp—X)$_n$ and/or n is 1, c) in case m1+m2 is 2, then A$^1$ and A$^2$ are not cyclohexylene.

Another object of the invention is a polymerizable liquid crystal composition comprising at least two polymerizable components, at least one of which is a compound of formula I.

Another object of the invention is a linear or crosslinked polymer obtainable by polymerization of one or more compounds of formula I or of a polymerizable composition comprising one or more compounds of formula I.

Yet another object of the invention is the use of a compound of formula I, or a polymerizable composition or polymer obtainable thereof, in optical elements such as polarizers, optical retardation or compensation films, alignment layers, colour filters or holographic elements, in liquid crystal displays such as PDLC (polymer dispersed liquid crystals), polymer gel or polymer stabilized cholesteric texture (PSCT) displays, in adhesives, synthetic resins with anisotropic mechanical properties, cosmetics, diagnostics or liquid crystal pigments, for decorative and security applications, and for nonlinear optics or optical information storage.

Especially preferred are compounds of formula I wherein
m1+m2≧1
at least one of A$^1$ and A$^2$ is an aryl group as previously described, preferably when m1+m2=1,
one of m1 and m2 is 1 and the other is 0,
m1 is 1 and m2 is 0,
at least one of Z$^1$ and Z$^2$ is —COO— or —OCO—,
R has one of the meanings given for P—(Sp—X)$_n$—,
R is halogen, cyano or an optionally fluorinated achiral or chiral alkyl or alkoxy group with 1 to 15 C atoms,
n is 1,
Sp is alkylene with 1 to 12 C atoms,
X is —O— or a single bond.

Of the compounds of formula I wherein P is CH$_2$=CW—COO— especially preferred are those wherein n is 1.

Of the compounds of formula I wherein m1+m2 is 1 or 2, especially preferred are those wherein n is 1, those wherein one or both of Z$^1$ and Z$^2$ are an ester group, and those wherein R is P—(Sp—X)$_n$—.

Of the compounds of formula I wherein m1+m2 is 2 especially preferred are those wherein A$^1$ and A$^2$ are substituted or unsubstituted 1,4-phenylene in which, in addition, one or more CH groups may be replaced by N.

Of the polymerizable mesogenic compounds of formula I especially preferred are those wherein —(A$^1$—Z$^1$)$_{m1}$— and —(Z$^2$—A$^2$)$_{m2}$— are, each independently, denoting a group with one or two six-membered rings.

The groups —(A$^1$—Z$^1$)$_{m1}$— and —(Z$^2$—A$^2$)$_{m2}$— may be identical or different. Particularly preferred are compounds wherein —(A$^1$—Z$^1$)$_{m1}$— and —(Z$^2$—A$^2$)$_{m2}$— are different.

Preferred subformulae for the groups —(A$^1$—Z$^1$)$_{m1}$— and —(Z$^2$—A$^2$)$_{m2}$— are listed below. For reasons of simplicity, Phe in these groups is 1,4-phenylene, Phe L is a 1,4-phenylene group which is substituted by 1 to 4 groups L, with L being F, Cl, CN, OH, NO$_2$ or an optionally fluorinated or optionally chlorinated alkyl, alkoxy or alkanoyl group with 1 to 7 C atoms, and Cyc is 1,4-cyclohexylene. The following list of preferred groups —(A$^1$—Z$^1$)$_{m1}$— and —(Z$^2$—A$^2$)$_{m2}$— is comprising the subformulae II-1 to II-9 as well as their mirror images, which are linked via the radical Z to the tolane group in formula I

| | |
|---|---|
| -Phe-Z— | II-1 |
| -Cyc-Z— | II-2 |
| -PheL-Z— | II-3 |
| -Phe-Z-Phe-Z— | II-4 |
| -Phe-Z-Cyc-Z— | II-5 |
| -Cyc-Z-Cyc-Z— | II-6 |
| -PheL-Z-Phe-Z— | II-7 |
| -PheL-Z-Cyc-Z— | II-8 |
| -PheL-Z-PheL-Z— | II-9 |

Particularly preferred are the subformulae II-1, II-3, II-7 and II-8.

In these preferred groups Z has the meaning of Z$^1$ as given in formula I. Preferably Z is —COO—, —OCO—, —CH$_2$CH$_2$— —C≡C— or a single bond.

Very preferably —(A$^1$—Z$^1$)$_{m1}$— and —(Z$^2$—A$^2$)$_{m2}$— are, independently of each other, selected from the following formulae and their mirror images, which are linked via the radical Z to the tolane group in formula I

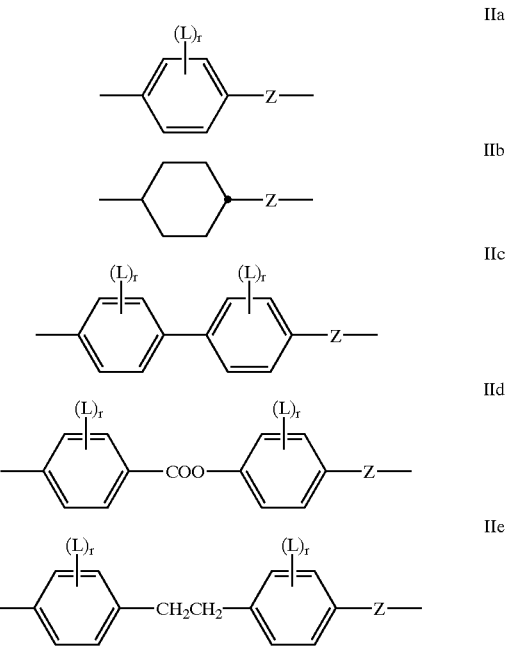

-continued

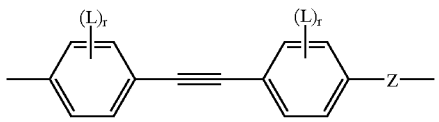
IIf wherein Z and L have the meaning given above and r is 0, 1, 2, 3 or 4, preferably 0, 1 or 2.

The group

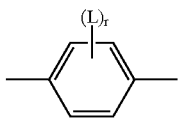

in these preferred formulae is very preferably denoting

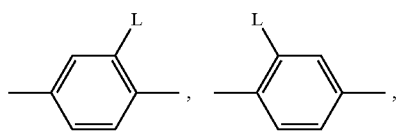

or

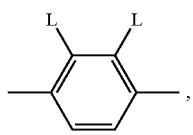

furthermore

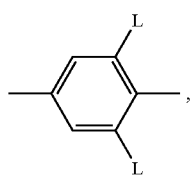

with L having each independently one of the meanings given above.

Particularly preferred are the subformulae IIa, IIc and IIf, in particular the subformulae IIa, IId and IIf.

Especially preferred are compounds of formula I comprising at least one group

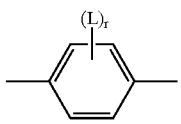

wherein r is 1.

Further preferred are compounds of formula I comprising at least two groups

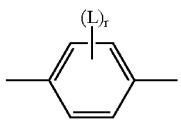

wherein r is 1 and/or at least one group

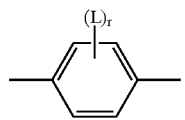

wherein r is 2.

L is preferably F, Cl, CN, OH, NO$_2$, CH$_3$, C$_2$H$_5$, OCH$_3$, OC$_2$H$_5$, COCH$_3$, COC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, Cl, CH$_3$, OCH$_3$ and COCH$_3$.

L$^1$ and L$^2$ in formula I preferably denote, independently of each other, F, Cl, CN, OH, NO$_2$, CH$_3$, C$_2$H$_5$, OCH$_3$, OC$_2$H$_5$, CF$_3$, OCF$_3$, OCHF$_2$ or OC$_2$F$_5$, in particular F, Cl, OCH$_3$ or OCF$_3$, most preferably F, Cl or OCH$_3$. r is preferably 0, 1 or 2, most preferably 0 or 1.

If R in formula I is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In the compounds of formula I R may be an achiral or a chiral group. In case of a chiral group it is preferably selected according to the following formula III:

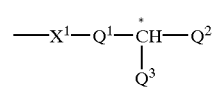
III wherein

X$^1$ is —O—, —S—, —CO—, —COO—, —OCO—, —OCOO— or a single bond,

Q$^1$ is an alkylene or alkylene-oxy group with 1 to 10 C atoms or a single bond, Q$^2$ is an alkyl or alkoxy group with 1 to 10 C atoms which may be unsubstituted, mono- or polysubstituted by halogen or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another, Q$^3$ is halogen, a cyano group or an alkyl or alkoxy group with 1 to 4 C atoms different from Q$^2$.

In case Q$^1$ in formula III is an alkylene-oxy group, the O atom is preferably adjacent to the chiral C atom.

Preferred chiral groups R are 2-butyl(=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy for example.

In addition, compounds of formula I containing an achiral branched group R may occasionally be of importance, for example, due to a reduction in the tendency towards crystallization. Branched groups of this type generally do not contain more than one chain branch. Preferred achiral branched groups are isopropyl, isobutyl(=methylpropyl), isopentyl(=3-methylbutyl), isopropoxy, 2-methylpropoxy and 3-methylbutoxy.

Very preferably R in formula I is halogen, cyano or an optionally fluorinated achiral or chiral alkyl or alkoxy group with 1 to 15 C atoms.

Another preferred embodiment of the present invention relates to compounds of formula I wherein R is P—(Sp—X)$_n$—.

P in formula I is preferably an acrylate group, a methacrylate group, a vinyl or vinyloxy group, an epoxy group, a styrene group or a propenyl ether group, in particular an acrylate, methacrylate, vinyl or epoxy group.

As for the spacer group Sp in formula I all groups can be used that are known for this purpose to the skilled in the art. The spacer group Sp is preferably a linear or branched alkylene group having 1 to 25 C atoms, especially 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —CH(CN)—, —CH=CH— or —C≡C—.

Typical spacer groups are for example —($CH_2$)$_o$—, —($CH_2CH_2O$)$_p$—$CH_2CH_2$—, —$CH_2CH_2$—S—$CH_2CH_2$— or —$CH_2CH_2$—NH—$CH_2CH_2$—, with o being an integer from 2 to 12 and p being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene for example.

Especially preferred are inventive compounds of formula I wherein Sp is an alkylene or alkylene-oxy group with 2 to 8 C atoms. Straight-chain groups are especially preferred.

In another preferred embodiment of the invention the chiral compounds of formula I comprise at least one spacer group Sp that is a chiral group of the formula IV:

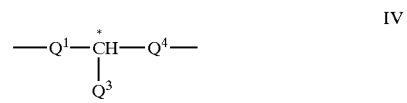

wherein $Q^1$ and $Q^3$ have the meanings given in formula III, and $Q^4$ is an alkylene or alkylene-oxy group with 1 to 10 C atoms or a single bond, being different from $Q^1$.

In the event that R is P—Sp—X—, the two spacer groups Sp in the compounds of formula I may be identical or different.

Of the preferred compounds described above particularly preferred are those wherein n is 1.

Further preferred are compounds comprising both a group P—(Sp—X)$_n$— wherein n is 0 and a group P—(Sp—X)$_n$— wherein n is 1.

X is preferably —O— or a single bond.

The inventive compounds of formula I can be synthesized according to or in analogy to methods which are known per se and which are described in standard works of organic chemistry such as, for example, Houben-Weyl, Methoden der organischen Chemie, Thieme-Verlag, Stuttgart. Some specific methods of preparation can be taken from the examples.

The invention also relates to a polymerizable liquid crystal composition comprising at least two polymerizable components, at least one of which is a compound of formula I, and to linear or crosslinked polymers prepared from the inventive compounds and compositions.

Suitable polymerizable mesogenic compounds that can be used as co-components of the polymerizable liquid crystal composition, together with the inventive compounds of formula I, are disclosed for example in WO 93/22397; EP 0,261,712; DE 195,04,224; WO 95/22586 and WO 97/00600. The compounds disclosed in these documents, however, are to be regarded merely as examples that shall not limit the scope of this invention.

Typical examples representing such polymerizable mesogenic compounds are shown in the following list of compounds, which should, however, be taken only as illustrative and is in no way intended to restrict, but instead to explain the present invention:

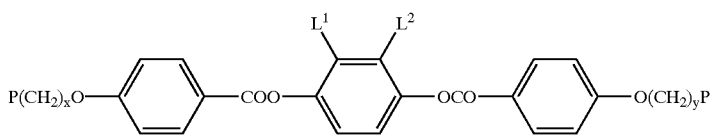

(V1)

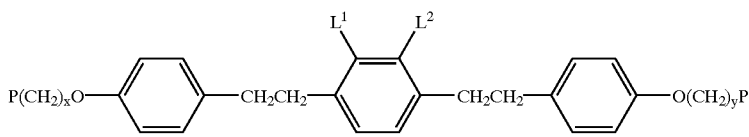

(V2)

-continued

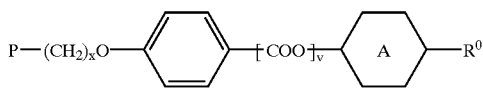
(V3)

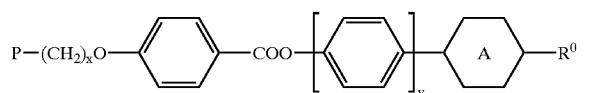
(V4)

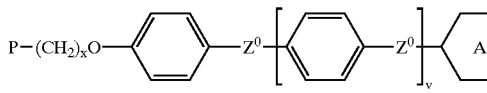
(V5)

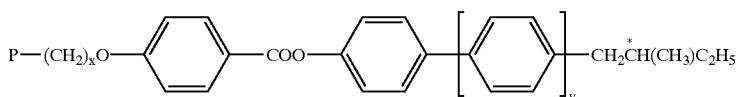
(V6)

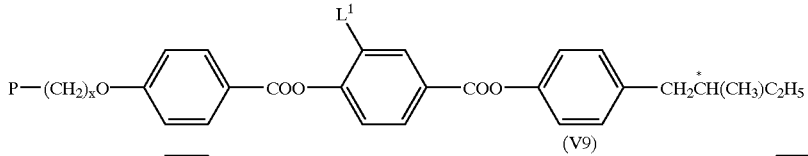
(V7)

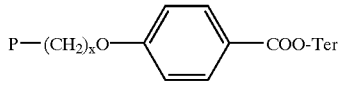
(V8)

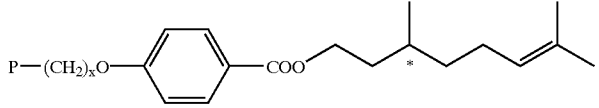
(V9)

(V10)

(V11)

In the above formulae, P has one of the meanings of formula I and its preferred meanings as mentioned above, x and y are each independently 1 to 12, A is 1,4-phenylene or 1,4-cyclohexylene, v is 0 or 1, $Z^0$ is —COO—, —OCO—, —CH$_2$CH$_2$— or a single bond, $R^0$ has one of the meanings of R in formula I and its preferred meanings as mentioned above, $L^1$ and $L^2$ have one of the meanings given above, Ter is terpene, and Chol is cholesterol.

In a preferred embodiment of the invention the polymerizable liquid crystalline composition comprises at least one monoreactive compound of formula I and at least one di- or multireactive polymerizable compound, i.e. a mesogenic compound having two or more polymerizable groups. Especially preferred are direactive compounds, i.e. compounds having two polymerizable groups. Very preferred are direactive compounds of formula I and of formulae V1 and V2 above.

It is also possible for the inventive polymerizable liquid crystalline composition to comprise one or more non-polymerizable chiral compounds, which may be mesogenic or non-mesogenic, in addition or alternatively to chiral polymerizable compounds. For example, commercially available dopants, like e.g. R 811 or R 1011 (from Merck KGaA, Germany) can be used for this purpose.

Especially preferred are chiral dopants of the following formulae

VI

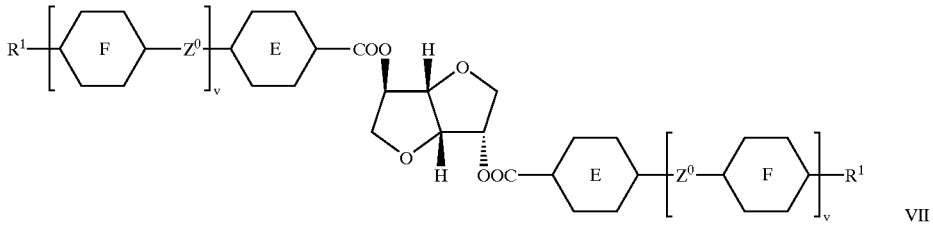

VII

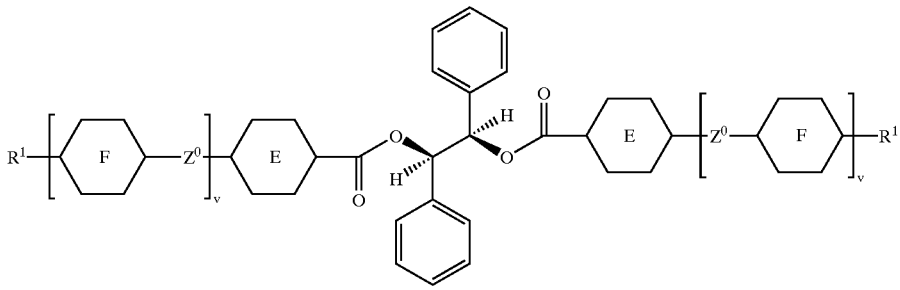

including the respective (R,R), (S,S), (S,R) and (R,S) enantiomers not shown, wherein E and F are each independently 1,4-phenylene or trans-1,4-cyclohexylene that may be substituted with $L^1$ as defined in formula 1, v is 0 or 1, $Z^0$ is —COO—, —OCO—, —CH$_2$CH$_2$— or a single bond, and $R^1$ is alkyl, alkoxy or alkanoyl with 1 to 12 C atoms.

The compounds of formula VI and their synthesis are described in WO 98/00428. The compounds of formula VII and their synthesis are described in GB 2,328,207. The above chiral compounds of formula VI and VII exhibit a very high helical twisting power (HTP), and are therefore particularly useful for the preparation of a CLC (cholesteric liquid crystal) polymer film with a short helical pitch.

Polymerizable liquid crystalline compositions are preferred that comprise 1 to 6, preferably 1 to 3 compounds of formula I.

In a preferred embodiment of the present invention the polymerizable liquid crystalline composition comprises 1 to 80% by weight, preferably 2 to 60%, in particular 5 to 50% by weight of one or more compounds of formula I.

Liquid crystalline polymers can be obtained from the inventive polymerizable compounds and compositions e.g. by solution polymerization or by in-situ polymerization.

For example, solution polymerization can be carried out in a solvent like dichloromethane, tetrahydrofuran or toluene using AIBN as an initiator and heating for 24 hours at 30 to 60° C.

The in-situ polymerization of polymerizable liquid crystalline compounds and compositions is described in detail by D. J. Broer et al., Makromol.Chem. 190, 2255ff. and 3202ff. (1989).

The polymerizable liquid crystal compounds and compositions according to this invention are preferably polymerized in situ as described in the foregoing and the following.

The inventive compounds and polymerizable liquid crystalline compositions are particularly useful for the preparation of anisotropic polymer films, such as nematic or cholesteric polymer films, with uniform molecular orientation.

Thus, another object of the invention is an anisotropic polymer film with an oriented liquid crystalline phase that is obtainable by polymerizing a polymerizable liquid crystalline composition comprising at least one compound of formula I.

To prepare an anisotropic polymer film with uniform orientation, an inventive polymerizable mesogenic composition is preferably coated onto a substrate, aligned and polymerized in situ by exposing them to heat or actinic radiation. Alignment and curing are preferably carried out in the liquid crystalline phase of the composition.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

When polymerizing by means of UV light, for example a photoinitiator can be used that decomposes under UV irradiation to produce free radicals or ions that start the polymerization reaction. It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1 173 or Darocure 4205 (all from Ciba Geigy AG) can be used, whereas in case of cationic photopolymerization the commercially available UVI 6974 (Union Carbide) can be used.

The polymerizable liquid crystalline composition preferably comprises 0.01 to 10%, in particular 0.05 to 8%, very preferably 0.1 to 5% by weight of a photoinitiator, especially preferably a UV-photoinitiator.

In addition to the components mentioned above, the polymerizable composition may also comprise one or more other suitable components such as e.g. catalysts, stabilizers, chain-transfer agents, co-reacting monomers or surface-active compounds. In particular the addition of stabilizers is preferred in order to prevent undesired spontaneous polymerization of the polymerizable material e.g. during storage.

As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

Other additives, like e.g. chain transfer agents, can also be added to the polymerizable material in order to modify the physical properties of the inventive polymer film. When adding a chain transfer agent, such as monofunctional thiol compounds like e.g. dodecane thiol or multifunctional thiol compounds like e.g. trimethylpropane tri(3-mercaptopropionate), to the polymerizable material, the length of the free polymer chains and/or the length of the polymer chains between two crosslinks in the inventive polymer film can be controlled. When the amount of the chain transfer agent is increased, the polymer chain length in the obtained polymer film is decreasing.

It is also possible, in order to increase crosslinking of the polymers, to add up to 20% of a non-mesogenic compound with two or more polymerizable functional groups to the polymerizable composition alternatively or additionally to the di- or multireactive mesogenic compounds.

Typical examples for difunctional non-mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

In a preferred embodiment of the invention the polymerization of the polymerizable composition is carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

In a preferred embodiment of the present invention, the inventive polymerizable composition is coated as a thin layer on a substrate or between two substrates and is aligned in its liquid crystal phase to give a uniform orientation.

A uniform orientation can be achieved for example by shearing the mixture, e.g. by means of a doctor blade. It is also possible to apply an alignment layer, for example a layer of rubbed polyimide or sputtered $SiO_x$, on top of at least one of the substrates. In some cases, the mixtures orient themselves spontaneously on the substrate, or good alignment is achieved already by the act of coating the mixture.

In another preferred embodiment, a second substrate is put on top of the coated material. In this case, the shearing caused by putting together the two substrates is sufficient to give good alignment.

It is also possible to apply an electric or magnetic field to align the coated mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinitiator oxygen exclusion most often is not needed, but water should be excluded.

For the preparation of anisotropic polymer gels, e.g. for use in switchable liquid crystal display devices, the polymerizable compounds or compositions can be polymerized in situ as described above, however, in this case alignment of the polymerizable mixture is not necessarily required, although it may be desired for specific applications.

The invention also relates to the use of inventive compounds, compositions and polymers such as polarizers, optical retardation or compensation films, alignment layers, colour filters or holographic elements, in liquid crystal displays such as PDLC, polymer gel or polymer stabilized cholesteric texture (PSCT) displays, in adhesives, synthetic resins with anisotropic mechanical properties, cosmetics, diagnostics or liquid crystal pigments, for decorative and security applications, and for nonlinear optics or optical information storage. Inventive compounds comprising a chiral group can also be used as chiral dopants.

The inventive compounds of formula I are particularly suitable for the preparation of oriented liquid crystal polymer films that can be used as polarization or compensation films in liquid crystal displays.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire disclosures of all applications, patents and publications, cited above and of corresponding European patent application No. 99112455.3, filed Jun. 30, 1999, are hereby incorporated by reference.

EXAMPLES

In the foregoing and in the following examples, unless otherwise indicated, all temperatures are set forth uncorrected in degrees Celsius and all parts and percentages are by weight. The following abbreviations are used to illustrate the liquid crystalline phase behavior of the compounds: K=crystalline; N=nematic; S=smectic; Ch=cholesteric; I=isotropic. The numbers between the symbols indicate the phase transition temperatures in ° C. Unless otherwise indicated, the phase transition temperatures are measured at a concentration of 5–10% by weight in the commercially available nematic host mixture ZLI-4792 (Merck KGaA, Darmstadt, Germany).

Example 1

The compounds of formula (1) were prepared according to the following reaction scheme.

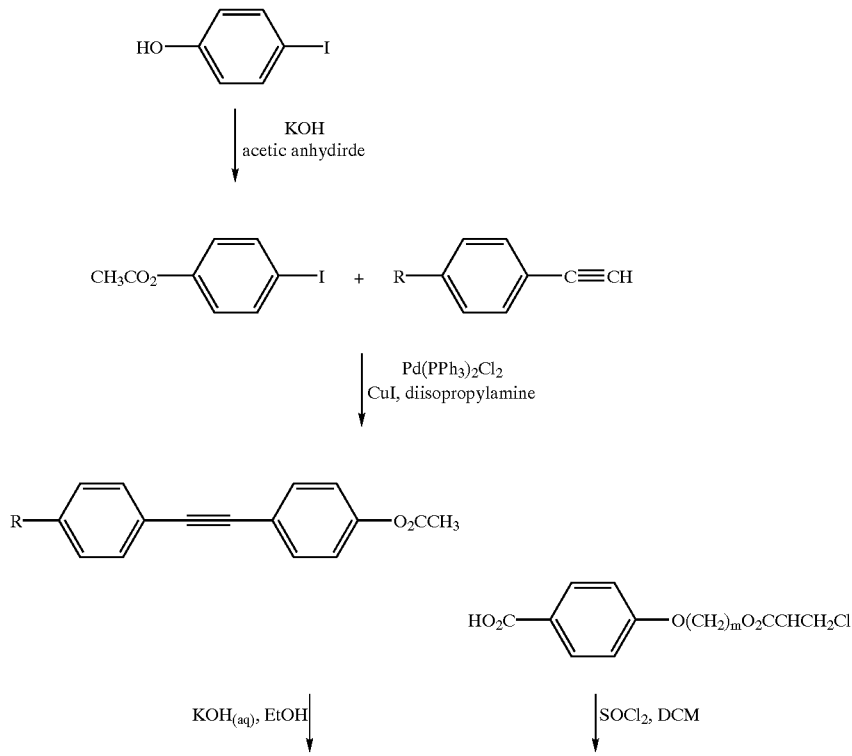

-continued

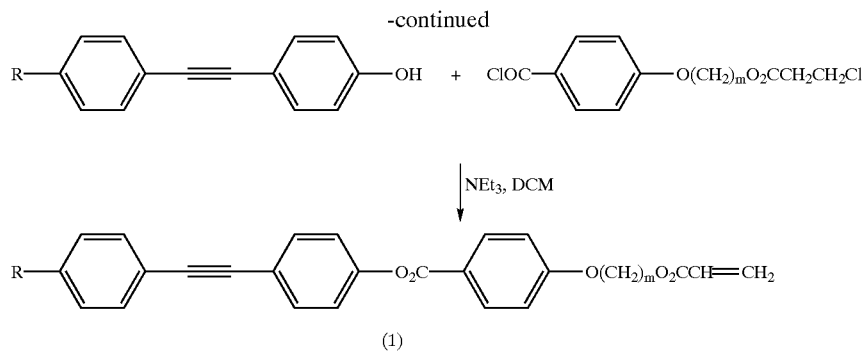

(1)

| Cpd. | R | m | LC phase behavior | Δn | ΔH (cal · mol$^{-1}$) | |
|---|---|---|---|---|---|---|
| 1 | $C_5H_{11}$ | 3 | K 83 N 165 I | 0.2577 | | |
| 2 | $C_5H_{11}$ | 6 | K 89 N 187 I | 0.2800 | K-I | 7418 |
| | | | | | N-I | 233 |

1-1) 4-Acetoxyphenyl iodide

4-Iodophenol (25.0 g, 13.6 mmol) was dissolved in a 3 molar aqueous solution of potassium hydroxide (56 ml, 170 mmol). Ice (150 g) was added, followed by acetic anhydride (16 ml, 170 mmol). The mixture was shaken vigorously for 2 minutes, transferred to a separating funnel and extracted with ethyl acetate (200 ml). The organic phase was removed, washed with water and dried ($Na_2SO_4$). Evaporation of the solution on a rotary evaporator left a residual brown oil. Purification by flash chromatography left a colourless liquid (eluant DCM). Yield=17.2 g, 72%. $^1$H-NMR and IR spectroscopy gave the expected signals.

1-2) 4-(4'-Pentylphenyl)ethynyl phenol

4-Pentylphenylacetylene (10.5 g, 61.4 mmol), 4-acetoxyphenyl iodide (16.1 g, 61.4 mmol), a catalytic amount of $Pd(PPh_3)_2Cl_2$ and a catalytic amount of copper iodide were stirred in diisopropylamine (100 ml) at 70° C. After 5 minutes, a precipitate was seen and the mixture became unstirrable, toluene (100 ml) was added. The mixture was stirred at room temperature for 24 hours and then evaporated to dryness on a rotary evaporator. The residue was redissolved in aqueous potassium hydroxide ethanolic solution and stirred at 70° C. overnight. The mixture was evaporated to dryness, then partitioned between ethyl acetate and water, the organic phase was removed, dried and evaporated. The residue was purified by flash column chromatography using DCM as eluant. A pink coloured solid was left after evaporation of the appropriate fractions. Yield= 10.4 g, 64%. $^1$H-NMR and IR spectroscopy gave the expected signals.

1-3) 4-(Oxyhexyl-3-chloropropanoyl)benzoyl chloride 4-(Oxypropyl-3-chloropropanoyl)benzoic acid (5.0 g, 17.4 mmol), thionyl chloride (1.65 ml, 22.6 mmol, 1.3 equivalents) and 3 drops N-methyl pyrollidone were stirred under reflux in DCM for 3 hours. The solution was cooled and evaporated to dryness to leave a colourless oil. Yield= 5.4 g, 100%. IR spectroscopy showed appropriate signals. The reagent was used without further purification in the next stage.

1-4) 4-Pentylphenyl ethynyl-4'-phenoxycarbonyl-4"-phenoxypropyl acrylate (1a)

The acid chloride of step 1-3) (5.3 g, 17.4 mmol), the phenol of step 1-2) (4.6 g, 17.4 mmol) and triethylamine (14.6 ml, 104.4 mmol, 6 equivalents) were stirred in DCM (150 ml) overnight at 35° C. The mixture was cooled to room temperature, washed with dilute aqueous hydrochlorid acid, water, and dried ($Na_2SO_4$), then evaporated to dryness on a rotary evaporator. The residue was purified by flash chromatography (eluant DCM:petrol 7:3) to give a white shiny solid. Yield=3.9 g, 86%. $^1$H-NMR and IR spectroscopy gave the expected signals.

Example 2

Further compounds of formula (1) were prepared according to the following reaction scheme.

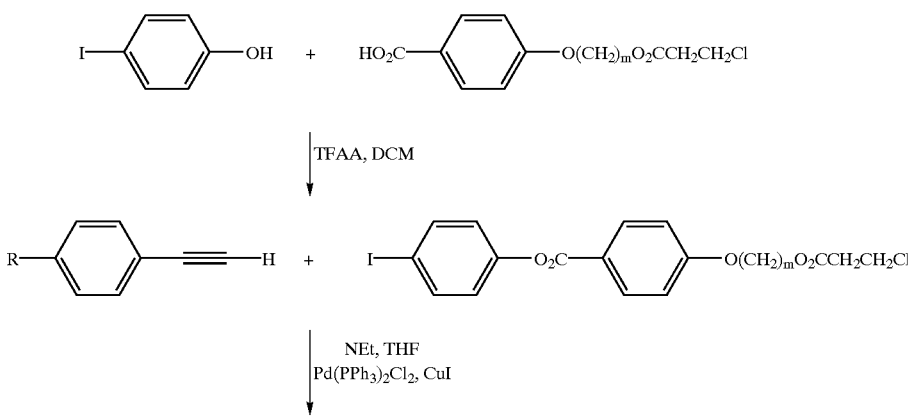

-continued

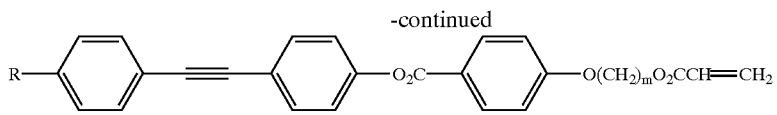

| Cpd. | R | m | LC phase behavior | Δn |
|---|---|---|---|---|
| 3 | $C_3H_7$ | 3 | K 86 N 1881 | 0.26 |
| 4 | $C_2H_5$ | 3 | K 99 N 1721 | 0.27 |
| 5 | $C_7H_{15}$ | 3 | K 88 N 1761 | 0.25 |
| 6 | $C_2H_5$ | 6 | K 94 N 1901 | 0.27 |
| 7 | $C_3H_7$ | 6 | K 83 N 1801 | 0.25 |
| 8 | $C_7H_{15}$ | 6 | K 80 N 1581 | 0.22 |
| 9 | $C_4H_9O$ | 3 | K 103 N 2031 | |
| 10 | $C_4H_9O$ | 6 | K 93 N 1951 | |
| 11 | $C_6H_{13}O$ | 6 | K 84 N 1851 | |
| 12 | $C_2H_5O$ | 6 | K 87 N 2131 | |
| 13 | $C_6H_{13}O$ | 3 | K 104 N 1981 | |

2-1) 4-Iodophenyl 4-[3-(3-chloropropanoyl)oxy]propoxybenzoate

4-[3-(3-Chloro-propanoyloxy)-propoxy]-benzoic acid (26.2 g, 91.0 mmol), 4-iodophenol (20.0 g, 91.0 mmol) and TFAA (22.9 g, 109.2 mmol) were dissolved in DCM (250 mL) and stirred under nitrogen for 3 hrs. The mixture was washed with dilute sodium hydrogen carbonate (2×200 mL), water (200 mL), dried ($Na_2SO_4$) and the solvent removed in vacuo to yield 4-Iodophenyl 4-[3-(3-chloropropanoyl)oxy]propoxybenzoate as a pale brown solid (41.8 g, 85.5 mmol, 94%). $^1H$ NMR and I.R. spectroscopy showed expected signals.

2-3) 4-[2-(4-propylphenyl)-1-ethynyl]phenyl 4-[3-(acryloyloxy)propoxy]benzoate

4-Iodophenyl-4-[3-(3-chloropropanoyl)oxy]propoxybenzoate (12.22 g, 25 mmol) and triethylamine (31 mL, 222 mmol) were stirred in THF (200 mL) under nitrogen for 24 hrs at room temperature. The mixture was cooled to −4° C. $Pd(PPh_3)_2Cl_2$ (cat.), copper iodide (cat.) and 4-propylphenylacetylene (4.0 g, 27 mmol) were added. The mixture was allowed to warm to room temperature and was then stirred for 48 hrs. Water (500 mL) was added followed by ethyl acetate (500 mL). The organic phase was washed with saturated sodium chloride (500 mL), dilute hydrochloric acid (4×500 mL), water (500 mL), saturated sodium chloride (500 mL) and dried ($Na_2SO_4$). The solvent was removed in vacuo to yield a yellow solid, this was purified by flash chromatography (3:1 DCM/petroleum ether) and recrystallisation from petroleum ether/ethyl acetate to yield 3 as a white solid (7.47 g, 15.1 mmol, 63.7%). Transition Temperatures: K-86-N-188-I; Δn=0.26; I.R. ($cm^{-1}$) 2956 (w), 2869 (w), 1741 (s); $\delta_H$ ($CDCl_3$): 8.17 (2H, d, J=9), 7.59 (2H, d, J=9), 7.47 (2H, d, J=8), 7.22 (2H, d, J=8), 7.18 (2H, d, J=8), 7.01 (2H, d, J=9), 6.45 (1H, dd, J=18, 1), 6.16 (1H, dd, J=18, 10), 5.87 (1H, dd, J=10, 1), 4.40 (2H, t, J=7), 4.18 (2H, t, J=7), 2.62 (2H, t, J=7), 2.23 (2H, quin, J=6), 1.73–1.61 (2H, m) 0.96 (3H, t, J=7). m/z (EI) 469 ($M^+$).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A polymerizable mesogenic tolane of formula I

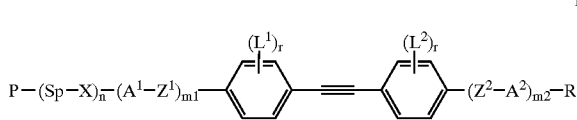

wherein

P is $CH_2$=CW—COO—, WCH=CH—O—,

or $CH_2$=CH-Phenyl-$(O)_k$—;

W is H, $CH_3$, or Cl;

k is 0 or 1;

Sp is a spacer group having 1 to 25 C atoms;

X is —O—, —S—, —CO—, —COO—, —OCO—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C—, or a single bond;

n is 0 or 1;

$Z^1$ and $Z^2$ are each independently —COO—, —OCO—, —$CH_2CH_2$—, —$OCH_2$—, —$CH_2O$—, —CH=CH—, —CH=CH—COO—, —OCO—CH=CH—, —C≡C—, or a single bond;

$A^1$ and $A^2$ are each independently 1,4-phenylene, 1,4-phenylene in which one or more CH groups are replaced by N, 1,4-cyclohexylene 1,4-cyclohexylene in which one or two non-adjacent $CH_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, $NO_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;

m1 and m2 are each independently 0, 1 or 2, with m1+m2<3;

$L^1$ and $L^2$ are each independently F, Cl, CN, OH, $NO_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and

R is H, CN, halogen or a straight-chain or branched alkyl radical with up to 25 C atoms which is unsubstituted, or mono- or polysubstituted by halogen or CN, and optionally one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:

a) when P is CH$_2$=CW—COO— or

and m1+m2 is 0, then R is P—(Sp—X)$_n$—, at least one r is different from 0, or both;

b) when P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then R is P—(Sp—X)$_n$, n is 1, or both; and c) when m1+m2 is 2, then neither A$^1$ nor A$^2$ are cyclohexylene;

d) when P is CH$_2$=CW—COO—, m1+m2 is 0, R is P—(Sp—X)$_n$, both n are 1, and both r are 1, then at least one of L$^1$ and L$^2$ is not F.

2. A polymerizable mesogenic tolane according to claim 1, wherein one or both of —(A$^1$—Z$^1$)$_{m1}$— and —(Z$^2$—A$^2$)$_{m2}$— are, independently of each other, selected from formulae IIa–IIf and their mirror images, which are linked via Z to the tolane group in formula I,

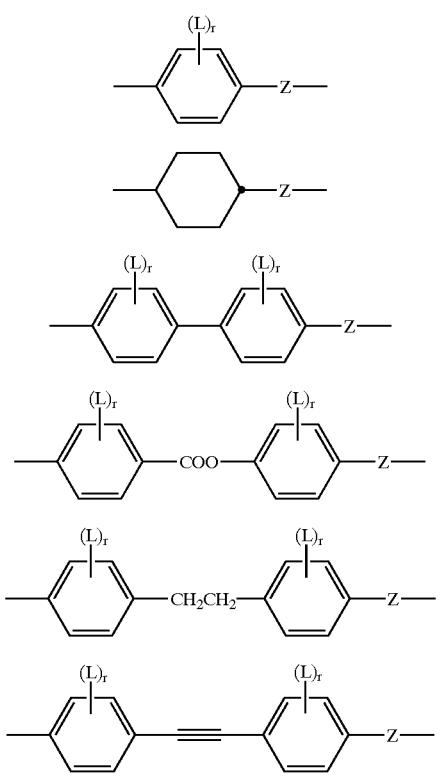

wherein

Z is —COO—, —OCO—, —CH$_2$CH$_2$—, —OCH$_2$—, —CH$_2$O—, —CH=CH—, —CH=CH—COO—, —OCO—CH=CH—, —C≡C—, or a single bond, L in each case independently is halogen, CN, OH, NO$_2$ or an alkyl, alkoxy or alkanoyl group having 1 to 7 C atoms, wherein one or more H atoms may be, in each case, replaced by F or Cl, and r is 0, 1, 2, 3 or 4.

3. A polymerizable mesogenic tolane according to claim 1, wherein m1 is 1 and m2 is 0.

4. A polymerizable mesogenic tolane according to claim 2, wherein m1 is 1 and m2 is 0.

5. A polymerizable mesogenic tolane according to claim 1, wherein P is an acryl, methacryl, vinyl or epoxy group.

6. A polymerizable mesogenic tolane according to claim 2, wherein P is an acryl, methacryl, vinyl or epoxy group.

7. A polymerizable mesogenic tolane according to claim 3, wherein P is an acryl, methacryl, vinyl or epoxy group.

8. A polymerizable mesogenic tolane according to claim 1, wherein R is P—(Sp—X)$_n$—.

9. A polymerizable mesogenic tolane according to claim 8, wherein the two P—(Sp—X)$_n$— groups are different from one another.

10. A polymerizable mesogenic tolane according to claim 1, wherein n is 1 and

Sp is alkylene with 1 to 12 C atoms.

11. A polymerizable tolane according to claim 1, wherein R is a chiral group of formula III having up to 25 C atoms

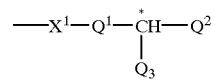

wherein

X is —O—, —S—, —CO—, —COO—, —OCO—, —OCOO— or a single bond,

Q$^1$ is an alkylene or alkylene-oxy group with 1 to 10 C atoms or a single bond, Q$^2$ is an alkyl or alkoxy group with 1 to 10 C atoms which may be unsubstituted, mono- or polysubstituted by halogen or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another, and Q$^3$ is halogen, a cyano group or an alkyl or alkoxy group with 1 to 4 C atoms which is different from Q$^2$.

12. A polymerizable liquid crystal composition comprising at least two polymerizable components, wherein at least one of said components is a compound according to claim 1.

13. A composition according to claim 12, wherein said composition contains at least one polymerizable mesogenic compound having two or more polymerizable terminal groups.

14. A linear or crosslinked polymer obtainable by polymerization of at least one compound according to claim 1.

15. A linear or crosslinked polymer obtainable by polymerization of a composition according to claim 12.

16. In a liquid crystal display, the improvement wherein said display contains one or more tolanes according to claim 1.

17. In a liquid crystal display, the improvement wherein said display contains one or more polymers according to claim 14.

18. In an optical element containing a mesogenic material, the improvement wherein one or more tolanes according to claim 1 form at least a part of said mesogenic material.

19. In an optical element containing a mesogenic material, the improvement wherein a composition according to claim 12 forms at least a part of said mesogenic material.

20. In an optical element containing a mesogenic material, the improvement wherein said mesogenic material contains at least one polymer according to claim 14.

21. A polymerizable mesogenic tolane of formula I

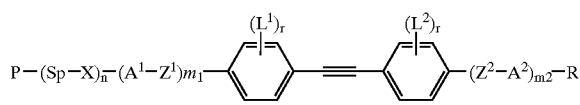

wherein
P is CH$_2$=CW—COO—, WCH=CH—O—,

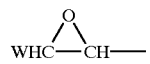

or CH$_2$=CH-Phenyl-(O)$_k$—;
W is H, CH$_3$, or Cl,
k is 0 or 1;
Sp is a spacer group having 1 to 25 C atoms;
X is —O—, —S—, —CO—, —COO—, —OCO—, —CO—NH—, —NH—CO—, —CH$_2$CH$_2$—, OCH$_2$—, —CH$_2$O, —SCH$_2$—, —CH$_2$S—, —CH=CH—, —CH=CH—COO—, —OCO—CH=CH—, —C≡C—, or a single bond;
n is 0 or 1,
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced in each case by N, 1,4-cyclohexylene, 1,4-cyclohexylene in which one or two nonadjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl group having 1 to 7 C atoms wherein one or more H atoms is replaced in each case by F or Cl, or combinations thereof,
m1 is 1; m2 is o;
L$^1$ and L$^2$ are each independently F, Cl, CN, OH, NO$_2$, or an alkyl, alkoxy or alkanoyl group having 1 to 7 C atoms, or an alkyl, alkoxy, or alkanoyl group having 1 to 7 C atoms, wherein one or more H atoms is replaced in each case by F or Cl,
r is in each case independently 0, 1, 2, 3 or 4, and
R is H, CN, halogen, or a straight-chain or branched alkyl radical with up to 25 C atoms which is unsubstituted, or mono- or polysubstituted by halogen or CN, and optionally one or more non-adjacent CH$_2$ groups is replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—, with the proviso that:
when P is CH$_2$=CW—COO— and one of —(A$^1$—Z$^1$)$_{m1}$— and —(A$^2$—Z$^2$)$_{m2}$— is substituted or umsubstituted phenylene and the other is a single bond, then R is P—(Sp—X)$_n$—, n is 1, or both.

22. A polymerizable mesogenic tolane of formula I

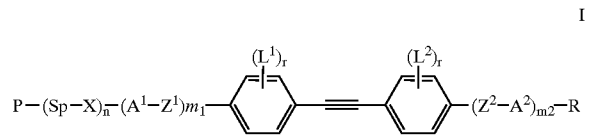

wherein
P is CH$_2$=CW—COO—, WCH=CH—O—,

or CH$_2$=CH-Phenyl-(O)$_k$—,
W is H, CH$_3$, or Cl,
k is 0 or 1;
Sp is a spacer group having 1 to 25 atoms;
X is —O—, —S—, —CO—, —COO—, —OCO—, —CO—NH—, —NH—CO—, —CH$_2$CH$_2$—, OCH$_2$—, —CH$_2$O, —SCH$_2$—, —CH$_2$S—, —CH=CH—, —CH=CH—COO—, —OCO—CH=CH—, —C≡C—, or a single bond;
n is 0 or 1,
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced in each case by N, 1,4-cyclohexylene, 1,4-cyclohexylene in which one or two nonadjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl group having 1 to 7 C atoms wherein one or more H atoms is replaced in each case by F or Cl, or combinations thereof,
m1 and m2 are each independently 0, 1 or 2, and m1+m2<3;
L$^1$ and L$^2$ are each independently F, Cl, CN, OH, NO$_2$, or an alkyl, alkoxy or alkanoyl group having 1 to 7 C atoms, or an alkyl, alkoxy, or alkanoyl group having 1 to 7 C atoms, wherein one or more H atoms is replaced in each case by F or Cl,
r is in each case independently 0, 1, 2, 3 or 4, and R is a chiral group of formula III having up to 25 C atoms

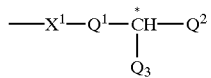

wherein
- X is —O—, —S—, —CO—, —COO—, —OCO—, —OCOO— or a single bond,
- $Q^1$ is an alkylene or alkylene-oxy group with 1 to 10 C atoms or a single bond,
- $Q^2$ is an alkyl or alkoxy group with 1 to 10 C atoms which may be unsubstituted, mono- or polysubstituted by halogen or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, and
- $Q^3$ is halogen, a cyano group or an alkyl or alkoxy group with 1 to 4 C atoms which is different from $Q^2$, with the provisos that:
- a) when P is $CH_2$=CW—COO— or

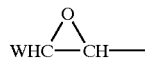

and m1+m2 is 0, then, at least one r is different from 0;
- b) when P is $CH_2$=CW—COO— and one of —($A^1$—$Z^1$)$_{m1}$— and —($A^2$—$Z^2$)$_{m2}$— is substituted or unsubstituted phenylene and the other is a single bond, then, n is 1; and
- c) when m1+m2 is 2, then $A^1$ and $A^2$ are not both cyclohexylene.

23. A polymerizable mesogenic tolane of formula I

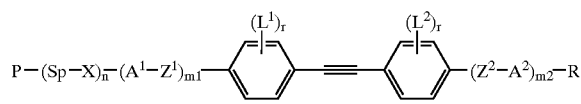

I wherein
P is $CH_2$=CW—COO—, WCH=H—O—,

or $CH_2$=CH-Phenyl-(O)$_k$—;
W is H, $CH_3$, or Cl;
k is 0 or 1;
Sp is a spacer group having 1 to 25 C atoms;
X is —O—, —S—, —CO—, —COO—, —OCO—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C—, or a single bond;
n is 0 or 1;
$Z^1$ and $Z^2$ are each independently —COO—, —OCO—, —$CH_2CH_2$—, —$OCH_2$—, —$CH_2O$—, —CH=CH—, —CH=CH—COO—, —OCO—CH=CH—, —C≡C—, or a single bond;

$A^1$ and $A^2$ are each independently 1,4-phenylene, 1,4-phenylene in which one or more CH groups are replaced by N, 1,4-cyclohexylene 1,4-cyclohexylene in which one or two non-adjacent $CH_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, $NO_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;

m1 and m2 are each independently 0, 1 or 2, with m1+m2<3;

$L^1$ and $L^2$ are each independently F, Cl, CN, OH, $NO_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and

R is H, CN, halogen or a straight-chain or branched alkyl radical with up to 25 C atoms which is unsubstituted, or mono- or polysubstituted by halogen or CN, and optionally one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:
- a) when P is $CH_2$=CW—COO— or

and m1+m2 is 0, then R is P—(Sp—X)$_n$—, at least one r is different from 0, or both;
- b) when P is $CH_2$=CW—COO— and one of —($A^1$—$Z^1$)$_{m1}$— and —($A^2$—$Z^2$)$_{m2}$— is substituted or unsubstituted phenylene and the other is a single bond, then R is P—(Sp—X)$_n$, n is 1, or both; and
- c) when m1+m2 is 2, then $A^1$ and $A^2$ are substituted 1,4-phenylene in which one or more CH groups are each optionally replaced by N;
- d) when P is $CH_2$=CW—COO—, m1+m2 is 0, R is P—(Sp—X)$_n$, both n are 1, and both r are 1, then at least one of $L^1$ and $L^2$ is not F.

24. A polymerizable mesogenic tolane of formula I

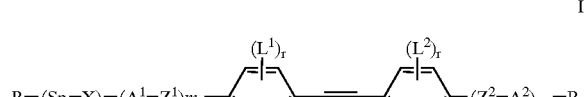

I wherein

P is CH$_2$=CW—COO—, WCH=CH—O—,

or CH$_2$=CH-Phenyl-(O)$_k$—;
W is H, CH$_3$, or Cl,
k is 0 or 1;
Sp is a spacer group having 1 to 25 C atoms;
X is —O—, —S—, —CO—, —COO—, —OCO—, —CO—NH—, —NH—CO—, —CH$_2$CH$_2$—, OCH$_2$—, —CH$_2$O, —SCH$_2$—, —CH$_2$S—, —CH=CH—, —CH=CH—COO—, —OCO—CH=CH—, —C≡C—, or a single bond;
n is 0 or 1,
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced in each case by N, 1,4-cyclohexylene, 1,4-cyclohexylene in which one or two nonadjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl group having 1 to 7 C atoms wherein one or more H atoms is replaced in each case by F or Cl, or combinations thereof,
m1 and m2 are each independently 0, 1 or 2, and m1+m2<3;
L$^1$ and L$^2$ are each independently F, Cl, CN, OH, NO$_2$, or an alkyl, alkoxy or alkanoyl group having 1 to 7 C atoms, or an alkyl, alkoxy, or alkanoyl group having 1 to 7 C atoms, wherein one or more H atoms is replaced in each case by F or Cl,
r is in each case independently 0, 1, 2, 3 or 4, and
R is H, CN, halogen, or a straight-chain or branched alkyl radical with up to 25 C atoms which is unsubstituted, or mono- or polysubstituted by halogen or CN, and optionally one or more non-adjacent CH$_2$ groups is replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another,
with the provisos that:
a) when P is CH$_2$=CW—COO— or

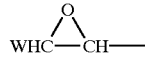

and m1+m2 is 0, at least one r is different from 0;
b) when P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then n is 1; and
c) when m1+m2 is 2, then A$^1$ and A$^2$ are not both cyclohexylene.

25. A polymerizable tolane according to claim 1, wherein Sp is a linear or branched alkylene group having 1–25 C atoms in which, in addition, one or more non-adjacent CH$_2$ groups may be replaced by —O—, —S—, —NH—, —N(CH$_3$)—, —CO—, —O—CO—, —S—CO—, —O—COO—, —CO—S—, —CO—O, —CH(halogen)-, —CH(CN)—, —CH=CH— or —C≡C—.

26. A polymerizable tolane compound according to claim 1, wherein Sp is —(CH$_2$)$_o$—, —(CH$_2$CH$_2$O)$_p$—CH$_2$CH$_2$—, —CH$_2$CH$_2$—S—CH$_2$CH$_2$— or —CH$_2$CH$_2$—NH—CH$_2$CH$_2$—, with o being an interger from 2 to 12 and p being an integer from 1 to 3.

27. A polymerizable tolane according to claim 1, wherein R is halogen, cyano, or an optionally flurorinated achiral or chiral alkyl or alkoxy group, in each case having 1–15 C atoms.

28. A polymerizable mesogenic tolane of formula I

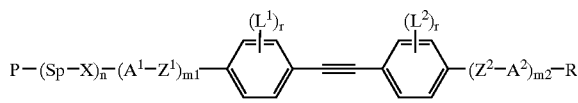

wherein
P is WCH=CH—O—,

or CH$_2$=CH-Phenyl-(O)$_k$—;
W is H, CH$_3$, or Cl;
k is 0 or 1;
Sp is a spacer group having 1 to 25 C atoms;
X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C—, or a single bond;
n is 0 or 1;
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced by N, 1,4-cyclohexylene 1,4-cyclohexylene in which one or two non-adjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;
m1 and m2 are each independently 0, 1 or 2, with m1+m2<3;
L$^1$ and L$^2$ are each independently F, Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and
R is H, CN, halogen or a straight-chain or branched alkyl radical with up to 25 C atoms which is unsubstituted, or mono- or polysubstituted by halogen or CN, and optionally one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:
a) when P is

and m1+m2 is 0, then R is P—(Sp—X)$_n$—, at least one r is different from 0, or both; and
b) when m1+m2 is 2, then neither $A^1$ nor $A^2$ are cyclohexylene.

29. A polymerizable mesogenic tolane of formula I

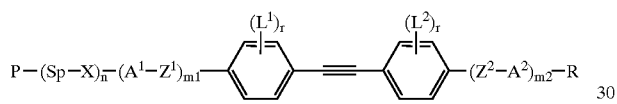

I wherein
P is $CH_2$=CW—COO—, WCH=CH—O—,

or $CH_2$=CH-Phenyl-(O)$_k$—;
W is H, $CH_3$, or Cl;
k is 0 or 1;
Sp is a spacer group having 1 to 25 C atoms;
X is —S—, —CO—, —COO—, —OCO—, —CO—NH—, —NH—CO—, —$CH_2CH_2$—, —$OCH_2$—, —$SCH_2$—, —$CH_2S$—, —CH=CH—, —CH=CH—COO—, —OCO—CH=CH—, —C≡C—, or a single bond;
n is 0 or 1;
$Z^1$ and $Z^2$ are each independently —COO—, —OCO—, —$CH_2CH_2$—, —$OCH_2$—, —$CH_2O$—, —CH=CH—, —CH=CH—COO—, —OCO—CH=CH—, —C≡C—, or a single bond;
$A^1$ and $A^2$ are each independently 1,4-phenylene, 1,4-phenylene in which one or more CH groups are replaced by N, 1,4-cyclohexylene 1,4-cyclohexylene in which one or two non-adjacent $CH_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, $NO_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;

m1 and m2 are each independently 0, 1 or 2, with m1+m2<3;
$L^1$ and $L^2$ are each independently F, Cl, CN, OH, $NO_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;
r is in each case independently 0, 1, 2, 3 or 4; and
R is H, CN, halogen or a straight-chain or branched alkyl radical with up to 25 C atoms which is unsubstituted, or mono- or polysubstituted by halogen or CN, and optionally one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:
a) when P is $CH_2$=CW—COO— or

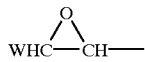

and m1+m2 is 0, then R is P—(Sp—X)$_n$—, at least one r is different from 0, or both;
b) when P is $CH_2$=CW—COO— and one of —($A^1$—$Z^1$)$_{m1}$— and —($A^2$—$Z^2$)$_{m2}$— is substituted or unsubstituted phenylene and the other is a single bond, then R is P—(Sp—X)$_n$, n is 1, or both; and
c) when m1+m2 is 2, then neither $A^1$ nor $A^2$ are cyclohexylene.

30. A polymerizable mesogenic tolane of formula I

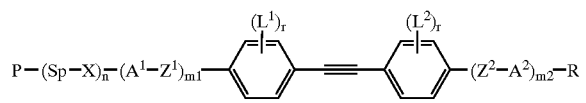

I wherein
P is $CH_2$=CW—COO—, WCH=CH—O—,

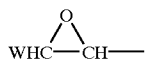

or $CH_2$=CH-Phenyl-(O)$_k$—;
W is H, $CH_3$, or Cl;
k is 0 or 1;
Sp is a spacer group having 1 to 25 C atoms;
X is —O—, —S—, —CO—, —COO—, —OCO—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C—, or a single bond;
n is 0 or 1;
$Z^1$ and $Z^2$ are each independently —COO—, —OCO—, —$CH_2CH_2$—, —$OCH_2$—, —$CH_2O$—, —CH=CH—, —CH=CH—COO—, —OCO—CH=CH—, —C≡C—, or a single bond;
$A^1$ and $A^2$ are each independently 1,4-phenylene, 1,4-phenylene in which one or more CH groups are replaced by N, 1,4-cyclohexylene 1,4-cyclohexylene in which one or two non-adjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;

m1 and m2 are each independently 0, 1 or 2, with m1+m2<3;

L$^1$ and L$^2$ are each independently F, Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and

R is H, CN, halogen or a straight-chain or branched alkyl radical with up to 25 C atoms which is unsubstituted, or mono- or polysubstituted by halogen or CN, and optionally one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another;

with the provisos that:

a) when P is CH$_2$=CW—COO— or

and m1+m2 is 0, then at least one r is different from 0;

b) when P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then n is 1; and c) when m1+m2 is 2, then neither A$^1$ nor A$^2$ are cyclohexylene.

31. A polymerizable mesogenic tolane of formula I

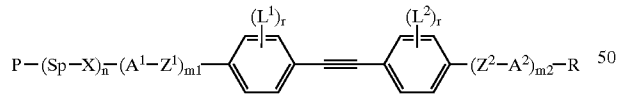

wherein

P is CH$_2$=CW—COO—, WCH=CH—O—,

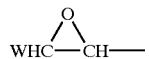

or CH$_2$=CH-Phenyl-(O)$_k$—;

W is H, CH$_3$, or Cl;

k is 0 or 1;

Sp is a spacer group having 1 to 25 C atoms;

X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C—, or a single bond;

n is 0 or 1;

Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;

A$^1$ and A$^2$ are each independently 1,4-phenylene, 1,4-phenylene in which one or more CH groups are replaced by N, 1,4-cyclohexylene 1,4-cyclohexylene in which one or two non-adjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;

m1 and m2 are each independently 0, 1 or 2, with m1+m2<3;

L$^1$ is Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

L$^2$ is F, Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and

R is H, CN, halogen or a straight-chain or branched alkyl radical with up to 25 C atoms which is unsubstituted, or mono- or polysubstituted by halogen or CN, and optionally one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:

a) when P is CH$_2$=CW—COO— or

and m1+m2 is 0, then R is P—(Sp—X)$_n$—, at least one r is different from 0, or both;

b) when P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then R is P—(Sp—X)$_n$, n is 1, or both; and c) when m1+m2 is 2, then neither A$^1$ nor A$^2$ are cyclohexylene.

32. A polymerizable mesogenic tolane of formula I

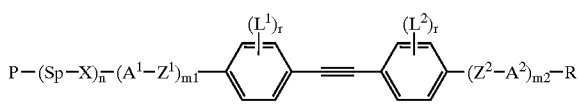

wherein
P is CH$_2$=CW—COO—, WCH=CH—O—,

or CH$_2$=CH-Phenyl-(O)$_k$—;
W is H, CH$_3$, or Cl;
k is 0 or 1;
Sp is a spacer group having 1 to 25 C atoms;
X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C—, or a single bond;
n is 0 or 1;
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced by N, 1,4-cyclohexylene 1,4-cyclohexylene in which one or two non-adjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;
m1 and m2 are each independently 0, 1 or 2, with m1+m2<3;
L$^1$ is F, Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;
L$^2$ is Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;
r is in each case independently 0, 1, 2, 3 or 4; and
R is H, CN, halogen or a straight-chain or branched alkyl radical with up to 25 C atoms which is unsubstituted, or mono- or polysubstituted by halogen or CN, and optionally one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:
a) when P is CH$_2$=CW—COO— or

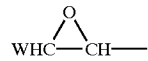

and m1+m2 is 0, then R is P—(Sp—X)$_n$—, at least one r is different from 0, or both;
b) when P is CH$_2$=CW—COO— and one of —(A$^1$—Z$^1$)$_{m1}$— and —(A$^2$—Z$^2$)$_{m2}$— is substituted or unsubstituted phenylene and the other is a single bond, then R is P—(Sp—X)$_n$, n is 1, or both; and
c) when m1+m2 is 2, then neither A$^1$ nor A$^2$ are cyclohexylene.

33. A polymerizable mesogenic tolane of formula I

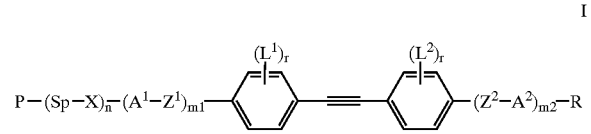

wherein
P is CH$_2$=CW—COO—, WCH=CH—O—,

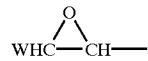

or CH$_2$=CH-Phenyl-(O)$_k$—;
W is H, CH$_3$, or Cl;
k is 0 or 1;
Sp is a spacer group having 1 to 25 C atoms;
X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH2S—, —CH=CH—, —CH=CH—COO—, —OCO—CH=CH—, —C≡C—, or a single bond;
n is 0 or 1;
Z$^1$ and Z$^2$ are each independently —COO—, —OCO—, —CH$_2$CH$_2$—, —OCH$_2$—, —CH$_2$O—, —CH=CH—, —CH=CH—COO—, —OCO—CH=CH—, —C≡C—, or a single bond;
A$^1$ and A$^2$ are each independently 1,4-phenylene, 1,4-phenylene in which one or more CH groups are replaced by N, 1,4-cyclohexylene 1,4-cyclohexylene in which one or two non-adjacent CH$_2$ groups are replaced in each case by O or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydro-naphthalene-2,6-diyl, wherein all these groups are unsubstituted, or mono- or polysubstituted with F, Cl, CN, OH, NO$_2$, alkyl, alkoxy or alkanoyl groups having 1 to 7 C atoms, alkyl, alkoxy or alkanoyl groups having 1 to 7 C atoms wherein one or more H atoms is replaced in each case by F or Cl, or combinations thereof;
m1 and m2 are each independently 0, 1 or 2, with m1+m2≧1 and m1+m2<3;
L$^1$ and L$^2$ are each independently F, Cl, CN, OH, NO$_2$, or an alkyl, alkoxy or alkanoyl group having 1 to 7 C atoms, or an alkyl, alkoxy or alkanoyl group having 1 to 7 C atoms, wherein one or more H atoms is replaced in each case by F or Cl;

r is in each case independently 0, 1, 2, 3 or 4; and

R is H, CN, halogen or a straight-chain or branched alkyl radical with up to 25 C atoms which is unsubstituted, or mono- or polysubstituted by halogen or CN, and optionally one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R has one of the meanings of P—(Sp—X)$_n$—;

with the provisos that:

a) when P is $CH_2$=CW—COO— and one of —($A^1$-$Z^1$)$_{m1}$— and —($A^2$—$Z^2$)$_{m2}$— is substituted or unsubstituted phenylene and the other is a single bond, then R is P—(Sp—X)$_n$, n is 1, or both; and b) when m1+m2 is 2, then neither $A^1$ nor $A^2$ are cyclohexylene.

34. A compound according to claim 4, wherein R is P—(Sp—X)$_n$—.

35. A compound according to claim 34, wherein of —($A^1$—$Z^1$)— is of formula IIa

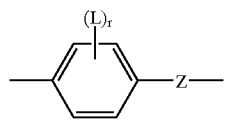

IIa and Z is —COO—, —OCO—, or —C≡C—.

36. A compound according to claim 35, wherein in at least one phenylene ring r is 1 or 2, and L, $L^1$, or $L^2$ is F, Cl, $CH_3$, $OCH_3$, or $COCH_3$.

37. A compound according to claim 1, wherein —($A^1$—$Z^1$)— is selected from formula II-1 to II-9

| | |
|---|---|
| -Phe-Z— | II-1 |
| -Cyc-Z— | II-2 |
| -PheL-Z— | II-3 |
| -Phe-Z-Phe-Z— | II-4 |
| -Phe-Z-Cyc-Z— | II-5 |
| -Cyc-Z-Cyc-Z— | II-6 |
| -PheL-Z-Phe-Z— | II-7 |
| -PheL-Z-Cyc-Z— | II-8 |
| -PheL-Z-PheL-Z— | II-9 | wherein

Phe is 1,4-phenylene,

Phe L is a 1,4-phenylene group which is substituted by 1 to 4 groups L,

L is F, Cl, CN, OH, $NO_2$ or an optionally fluorinated or optionally chlorinated alkyl, alkoxy or alkanoyl group with 1 to 7 C atoms, and Cyc is 1,4-cyclohexylene.

38. A compound according to claim 4, wherein $A^1$ is naphthalene-2,6-diyl.

39. A compound according to claim 4, wherein R is halogen, cyano, or an optionally flourinated achiral or chitral alkyl or alkoxy in each case having 1 to 15 C atoms.

40. A compound according to claim 4, wherein m1 is 1, m2 is 0, and R is halogen, cyano, or an optionally flourinated achiral or chitral alkyl or alkoxy in each case having 1 to 15 C atoms.

41. A polymerizable composition comprising at least two polymerizable components, at least one of which is a compound according to claim 4.

42. A polymerizable composition comprising at least two polymerizable components, at least one of which is a compound according to claim 35.

43. A polymerizable composition comprising at least two polymerizable components, at least one of which is a compound according to claim 27.

44. A polymerizable composition comprising at least two polymerizable components, at least one of which is a compound according to claim 39.

45. A linear or crosslinked polymer obtainable by polymerization of at least one compound according to claim 4.

46. A linear or crosslinked polymer obtainable by polymerization of at least one compound according to claim 35.

47. A linear or crosslinked polymer obtainable by polymerization of at least one compound according to claim 41.

48. A linear or crosslinked polymer obtainable by polymerization of at least one compound according to claim 43.

49. In a polarizer, optical retardation or compensation film, alignment or color filter comprising at least one mesogenic compound, the improvement wherein said compound is a compound according to claim 1.

50. In a polarizer, optical retardation or compensation film, alignment or color filter comprising at least one mesogenic compound, the improvement wherein said compound is a compound according to claim 4.

51. In a polarizer, optical retardation or compensation film, alignment or color filter comprising at least one mesogenic compound, the improvement wherein said compound is a compound according to claim 35.

52. In a polarizer, optical retardation or compensation film, alignment or color filter comprising at least one mesogenic compound, the improvement wherein said compound is a compound according to claim 33.

53. In a polarizer, optical retardation or compensation film, alignment or color filter comprising at least one mesogenic compound, the improvement wherein said compound is a compound according to claim 45.

54. In a polarizer, optical retardation or compensation film, alignment or color filter comprising at least one mesogenic compound, the improvement wherein said compound is a compound according to claim 15.

55. In a polarizer, optical retardation or compensation film, alignment or color filter comprising at least one mesogenic compound, the improvement wherein said compound is a compound according to claim 48.

* * * * *

UNITED STATES PATENT AND TRADEMARK OFFICE
CERTIFICATE OF CORRECTION

PATENT NO.    : 6,514,578 B1
DATED         : February 4, 2003
INVENTOR(S)   : Louise Farrand It is certified that error appears in the above-identified patent and that said Letters Patent is hereby corrected as shown below:

Title page,
Item [73], Assignee, "beshrankter," should read -- beshraenkter --

Column 20,
Line 28, reads "$Q_3$," should read -- $Q^3$ --

Column 21,
Line 53, reads "m2 is o;" should read -- m2 is 0; --

Column 22,
Line 8, reads "umsubstituted" should read -- unsubstituted --

Column 23,
Line 48, reads "WCH=H-O-," should read -- WCH=CH-O-, --

Column 25,
Line 13, reads "$OCH_2$-," should read -- $OCH_2$-, --
Line 33, reads "group having" should read -- groups having --

Column 26,
Line 6, reads "-CO-O," should read -- CO-O-, --
Line 11, reads "an interger from" should read -- an interger from --

Column 33,
Line 23, reads "wherein of" should read -- wherein --
Line 59, after "chlorinated" please delete the line break

UNITED STATES PATENT AND TRADEMARK OFFICE
CERTIFICATE OF CORRECTION

PATENT NO. : 6,514,578 B1
DATED : February 4, 2003
INVENTOR(S) : Louise Farrand

It is certified that error appears in the above-identified patent and that said Letters Patent is hereby corrected as shown below:

Column 34,
Lines 5 and 8, reads "flourinated" should read -- fluorinated --

Signed and Sealed this

Third Day of August, 2004

JON W. DUDAS
*Acting Director of the United States Patent and Trademark Office*